(12) United States Patent
Weissker et al.

(10) Patent No.: US 11,945,767 B2
(45) Date of Patent: Apr. 2, 2024

(54) METHOD FOR PRODUCING METAL ALCOHOLATES

(71) Applicant: BASF SE, Ludwigshafen am Rhein (DE)

(72) Inventors: Wolf-Steffen Weissker, Ludwigshafen am Rhein (DE); Nuria Huguet Subiela, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/785,674

(22) PCT Filed: Dec. 16, 2020

(86) PCT No.: PCT/EP2020/086362
§ 371 (c)(1),
(2) Date: Jun. 15, 2022

(87) PCT Pub. No.: WO2021/122702
PCT Pub. Date: Jun. 24, 2021

(65) Prior Publication Data
US 2023/0054206 A1    Feb. 23, 2023

(30) Foreign Application Priority Data
Dec. 18, 2019 (EP) ................................. 19217475

(51) Int. Cl.
C07C 29/70    (2006.01)
(52) U.S. Cl.
CPC .................. C07C 29/705 (2013.01)
(58) Field of Classification Search
CPC ....... C07C 29/705; C07C 31/10; C07C 31/12; C07C 31/125
See application file for complete search history.

(56) References Cited

U.S. PATENT DOCUMENTS 4,327,230 A * 4/1982 Ackermann .......... C07C 29/705
568/838

FOREIGN PATENT DOCUMENTS

DE    1254612 B    11/1967
DE    2726491 A1   12/1978
(Continued)

OTHER PUBLICATIONS

International Preliminary Report on Patentability received for PCT Patent Application No. PCT/EP2020/086362, dated Jun. 30, 2022, 14 pages (8 pages of English Translation and 6 pages of Original Document).

(Continued)

Primary Examiner — Yate' K Cutliff
(74) Attorney, Agent, or Firm — Faegre Drinker Biddle & Reath LLP

(57) ABSTRACT

Process for preparing metal alkoxides by means of transalcoholization, wherein a lower metal alkoxide is fed via a side feed into a reactive distillation column comprising a rectifying section situated above the feed and a stripping section situated below the feed; a higher alcohol is fed into the stripping section, the bottom and/or a bottoms circuit of the column; a solution of a higher metal alkoxide in the higher alcohol is taken off at the bottom of the column and/or from the bottoms circuit; and a vapor comprising lower alcohol is taken off at the top of the column, the vapor is at least partially condensed and a substream of the condensate is recycled to the top of the column as reflux. The process enables the preparation of metal alkoxides with a reduced energy requirement.

11 Claims, 2 Drawing Sheets

(56) References Cited

FOREIGN PATENT DOCUMENTS

| | | |
|---|---|---|
| DE | 246988 A1 | 6/1987 |
| EP | 0091425 A2 | 10/1983 |
| EP | 0776995 A1 | 6/1997 |
| EP | 1997794 A1 | 12/2008 |
| GB | 1123088 A | 8/1968 |

OTHER PUBLICATIONS

International Search Report and Written Opinion received for PCT Patent Application No. PCT/EP20/086362, dated Mar. 24, 2021, 11 pages. (8 pages of English Translation and 8 pages of Original Document).

* cited by examiner

METHOD FOR PRODUCING METAL ALCOHOLATES

CROSS-REFERENCE TO RELATED APPLICATIONS

This application is a national stage application (under 35 U.S.C. § 371) of PCT/EP2020/086362, filed Dec. 16, 2020, which claims benefit of European Application No. 19217475.3, filed Dec. 18, 2019, both of which are incorporated herein by reference in their entirety.

Metal alkoxides are used as strong bases in the synthesis of numerous chemicals, for example in the preparation of active agents for the pharmaceuticals and agricultural industries. Metal alkoxides are also used as catalysts in transesterification and amidation reactions.

Metal alkoxides (MOR) may be prepared according to the following reaction equation from metal hydroxides (MOH) and alcohols (ROH), which are guided in countercurrent in a reactive distillation column, with the water formed in the reaction being removed with the distillate:

$$\text{MOH} + \text{ROH} \rightleftharpoons \text{MOR} + \text{H}_2\text{O}$$

EP 0 091 425 A1 describes such a process, in which an aqueous alkali metal hydroxide is introduced into the rectifying section and a gaseous alcohol is introduced into the bottom of the column. Water is removed via the top of the column as an azeotrope and subjected to a separation. Similar processes are described in EP 1997 794 A1 and DD 246 988 A1.

Metal alkoxides may also be prepared by means of transalcoholization according to the following formula, in which alkoxides of low-boiling alcohols ($MOR^1$) are reacted with a higher-boiling alcohol ($R^2OH$) by means of reactive distillation to afford lower alcohols and alkoxides of higher-boiling alcohols:

$$\text{MOR}^1 + \text{R}^2\text{OH} \rightleftharpoons \text{MOR}^2 + \text{R}^1\text{OH}$$

Such a process is described, for example, in DE 27 26 491 and in DE 1 254 612. A mixture of the higher-boiling alcohol and of the alkoxide of the low-boiling alcohol is fed into the column.

The known processes for preparing mental alkoxides of higher-boiling alcohols, such as isopropanol or tert-butanol, have a high energy requirement. The object of the present invention is that of providing a process for preparing metal alkoxides having a reduced energy requirement.

The object is achieved by a process for preparing metal alkoxides by means of transalcoholization, wherein
a lower metal alkoxide is fed via a side feed into a reactive distillation column comprising a rectifying section situated above the feed and a stripping section situated below the feed;
a higher alcohol is fed into the stripping section, the bottom and/or a bottoms circuit of the column;
a solution of a higher metal alkoxide in the higher alcohol is taken off at the bottom of the column and/or from the bottoms circuit, preferably downstream of the evaporator; and
a vapor comprising lower alcohol is taken off at the top of the column, the vapor is at least partially condensed and a substream of the condensate is recycled to the top of the column as reflux.

In the process according to the invention, the lower metal alkoxide and the higher alcohol are transalcoholized in order to obtain the higher metal alkoxide and the lower alcohol. A vapor comprising lower alcohol is taken off at the top of the reactive distillation column and a solution of the higher metal alkoxide in the higher alcohol is taken off at the bottom of the column and/or from the bottoms circuit. A gaseous and a liquid fraction are therefore taken off. The degree of purity of the fractions obtained is decisive for the efficiency of the process and the usability of the fractions.

The vapor taken off at the top of the column is at least partially condensed and a substream of the condensate obtained is recycled to the top of the column as reflux. In the column, a gas phase and a liquid phase are in contact with one another and are guided in countercurrent with respect to one another. Mass transfer takes place between the gas phase and the liquid phase. The more volatile fractions accumulate towards the top of the column in the gas phase and the less volatile fractions accumulate towards the bottom of the column in the liquid phase.

The degree of purity in particular of the solution of the higher metal alkoxide taken off at the bottom and/or from the bottoms circuit can be adjusted, inter alia, by the reflux ratio at the top of the column. In general, a greater reflux ratio results in a higher degree of purity of the solution of the higher metal alkoxide.

It has been found that feeding in the higher alcohol below the feed of the lower metal alkoxide brings about a significantly lower contamination of the solution of the higher metal alkoxide with lower alcohol. In order to achieve the desired specifications, a lower reflux ratio and a reduced bottoms circuit is therefore necessary in the process according to the invention. Advantageously, the process according to the invention therefore has a significantly lower energy requirement for the same separation task.

The terms "lower" and "higher" alcohol mean lower-boiling alcohol and higher-boiling alcohol. It goes without saying that in the process according to the invention the higher alcohol ("transalcoholization alcohol") has a higher boiling point than the alcohol of the lower metal alkoxide. The process according to the invention is generally applicable to the reaction of metal alkoxides of lower alcohols with higher alcohols, provided that the alcohols can be distilled and that the solubility characteristics of the lower and higher metal alkoxides permit reaction in the liquid phase.

The lower metal alkoxide is fed into the reactive distillation column via a side feed. The term "side" is understood to mean that the feeding is effected below the column top and above the column bottom. The location of the feed for the lower metal alkoxide divides the column into a rectifying section (above the feed) and a stripping section (below the location of the feed). The transalcoholization takes place in the stripping section of the column.

The lower metal alkoxide is usually fed in as a solution in the lower alcohol, wherein the solution comprises 20% to 40% by weight of the lower metal alkoxide, preferably 25% to 35% by weight of the lower metal alkoxide, such as 28% to 32% by weight of the lower metal alkoxide, based on the total weight of the solution of the lower metal alkoxide.

The lower metal alkoxide is typically a metal alkoxide of a monohydric $C_1$-$C_4$ alcohol, i.e. methoxide, ethoxide, propoxide, butoxide and constitutional isomers thereof, including cyclic alkoxides. The lower metal alkoxide is particularly preferably metal methoxide or metal ethoxide, especially metal methoxide.

The lower metal alkoxide is typically an alkali metal alkoxide, preferably a sodium alkoxide or a potassium alkoxide.

The lower metal alkoxide is particularly preferably sodium methoxide or potassium methoxide, especially sodium methoxide.

The temperature of the solution of the lower metal alkoxide at the side feed is selected suitably so that the lower metal alkoxide always remains in solution. The temperature of the solution of the lower metal alkoxide is preferably at least 6° C., in particular at least 10° C. and particularly preferably at least 20° C., for example 25° C. or 30° C. The solution of the lower metal alkoxide can be preheated up to boiling point, for example in a heat exchanger in which the solution of the higher metal alkoxide taken off at the bottom of the column is simultaneously cooled. This is particularly advantageous in terms of energy.

A higher alcohol is fed into the stripping section, the bottom and/or a bottoms circuit of the reactive distillation column, preferably into the bottom and/or the bottoms circuit. The higher alcohol can be fed into the stripping section, the bottom or bottoms circuit of the column in liquid form or gas form. The higher alcohol is preferably fed into the stripping section, the bottom and/or bottoms circuit of the column in liquid form. Particularly preferably, the higher alcohol is fed into the bottom and/or the bottoms circuit, in particular the bottoms circuit of the column, in liquid form.

The reactive distillation column typically has an evaporator, preferably a circulation evaporator. In the evaporator, a substream of the solution of the higher-boiling metal alkoxide taken off at the bottom of the column is heated and at least in part recycled to the bottom of the column in gas form. Alternatively or additionally, the bottom is heated directly. A portion of the higher alcohol is in gas form in the reactive distillation column and rises towards the top of the column.

The higher alcohol is typically selected from monohydric $C_2$-$C_{10}$ alcohols, i.e. ethanol, propanol, butanol, pentanol, hexanol, heptanol, octanol, nonanol, decanol and the constitutional isomers thereof, including cyclic alcohols. In principle, it is also possible to use polyhydric $C_2$-$C_{10}$ alcohols such as diols, for example ethylene glycol, diethylene glycol, propanediol or butanediol.

The higher alcohol is particularly preferably selected from isopropanol, sec-butanol, 2-methyl-2-butanol, tert-butanol, 2-methyl-2-pentanol, 3-methyl-3-pentanol, 3-ethyl-3-pentanol, 2-methyl-2-hexanol and 3-methyl-3-hexanol. Very particular preference is given to isopropanol, 2-methyl-2-butanol, 3-methyl-3-pentanol and 3-ethyl-3-pentanol, especially to isopropanol and 2-methyl-2-butanol.

A solution of the higher metal alkoxide in the higher alcohol is taken off at the bottom of the column and/or from the bottoms circuit. The solution of the higher metal alkoxide taken off advantageously has only small amounts of lower alcohol, which enables an efficient process. The solution of the higher metal alkoxide preferably comprises not more than 1.0% by weight of the lower alcohol, particularly preferably not more than 0.5% by weight of the lower alcohol and very particularly preferably not more than 0.3% by weight of the lower alcohol, for example 0.01% to 0.20% by weight of the lower alcohol or 0.01% to 0.10% by weight of the lower alcohol, based on the total weight of the solution of the higher metal alkoxide taken off. The methanol concentration in the solution of the higher metal alkoxide may for example be determined by means of headspace analysis or by means of gas chromatography.

The solution of the higher metal alkoxide typically comprises 3% to 60% by weight of the higher metal alkoxide, preferably 5% to 55% by weight and particularly preferably 7% to 50% by weight of the higher metal alkoxide, for example 7% to 30% by weight, 7% to 25% by weight, 7% to 20% by weight or 7% to 15% by weight of the higher metal alkoxide, based on the total weight of the solution of the higher metal alkoxide taken off. The concentration of the higher metal alkoxide in the solution of the higher metal alkoxide can be determined for example by means of titration.

A vapor comprising lower alcohol is taken off at the top of the column. The vapor taken off essentially consists of lower alcohol and advantageously has only small amounts of higher alcohol, which enables an efficient process. The vapor is at least partially condensed ("top condensate"), wherein the top condensate preferably comprises not more than 1.0% by weight of the higher alcohol, particularly preferably not more than 0.6% by weight of the higher alcohol and very particularly preferably not more than 0.5% by weight of the higher alcohol, based on the total weight of the top condensate. The concentration of the higher alcohol in the top condensate can for example be determined by means of gas chromatography.

The lower metal alkoxide and the higher alcohol are brought into contact with one another in a reactive distillation column. The lower metal alkoxide and the higher alcohol are brought into contact in countercurrent. The higher alcohol is partly in gas form and rises in the column towards the top of the column, while the solution of the lower metal alkoxide falls towards the bottom of the column. The contact between gas phase and liquid phase results in the higher alcohol and the lower metal alkoxide being transalcoholized to afford the higher metal alkoxide and the lower alcohol.

The reactive distillation column used can be a conventional reactive distillation column. The column is selected for example from columns having random packings, columns having structured packings and tray columns, particularly preferably tray columns and columns having structured packings.

Installed in suitable tray columns are sieve trays, bubble-cap trays or valve trays, over which the liquid phase flows. The reactive distillation column of the process according to the invention preferably has trays as internals, for example selected from bubble-cap trays, valve trays, tunnel-cap trays and Thormann® trays.

Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pall ring, Hiflow ring, Intalox saddle and the like. The random packings can be introduced into the column in an ordered manner, or else randomly (as a bed). Possible materials include glass, ceramic, metal and plastics.

Structured packings are a further development of ordered random packings. They have a regular structure. As a result, it is possible in the case of structured packings to reduce pressure drops in the gas flow. There are various designs of structured packings, for example woven packings or sheet metal packings.

Preferably, the rectifying section of the column comprises structured packings, while the stripping section of the column comprises trays.

The top of the column refers to the region free of internals above the uppermost tray or above the uppermost packing layer. It is generally formed by a domed end (hood, e.g. dished end or torispherical end), which forms the closing element of the reactive distillation column.

The bottom of the column refers to the region free of internals below the lowermost tray or below the lowermost packing layer.

The suitable number of theoretical plates in the rectifying section depends on the difference in vapor pressures of the higher and the lower alcohol, with a higher number of theoretical plates being advantageous in the case of a smaller difference. The suitable number of theoretical plates in the stripping section depends on the difference in the vapor pressures of the higher and the lower alcohol and the equilibrium position of the reaction, with a higher number of theoretical plates being advantageous the more the equilibrium is on the side of the starting materials. The suitable number of theoretical plates both in the rectifying section and in the stripping section moreover depends on the degree of purity of bottom and top product to be achieved and the reflux amount used, with a higher number of theoretical plates being needed to achieve a higher purity for a given reflux amount.

The column can consist of a plurality of individual vessels or individual columns connected in series in the manner of a cascade. The individual vessels or individual columns are preferably arranged one above the other and may optionally be offset laterally from one another. In a further embodiment, the individual vessels or individual columns are arranged next to one another with the use of suitable pumping devices.

In both cases, it must be ensured by appropriate connection conduits and possibly conveying devices that the stripping section and rectifying section are directly coupled to one another and that the reflux of the rectifying section can have an advantageous effect on the transalcoholization taking place in the stripping section. The reaction section and the rectifying section are preferably arranged one above the other in a single column.

The vapor comprising lower alcohol that is taken off at the top of the column is at least partially condensed to obtain a top condensate. The condensation is preferably effected in one or more series-connected plate or shell and tube condensers or air coolers. Preference is given to using air coolers or shell and tube condensers or combinations thereof. The condensers may for example be cooled by means of air, cooling water or brine, depending on the design.

The vapor is preferably essentially completely condensed, for example to an extent of more than 98% by weight or more than 99% by weight, based on the total amount of the vapor.

A substream of the condensate obtained is recycled to the top of the column as reflux. The reflux ratio influences the purity of the gaseous fraction taken off and in particular of the liquid fraction taken off. The reflux ratio is understood to be the ratio of the substream of the condensate (kg/h) which is recycled to the column (reflux) and the substream of the condensate (kg/h) which is discharged from the process.

The reflux ratios mentioned are targeted to the use of monohydric, aliphatic or cycloaliphatic higher alcohols. For other higher alcohols, for example in the case of dihydric or polyhydric alcohols or in the case of alcohols other than aliphatic or cycloaliphatic alcohols, the reflux amount may possibly be higher. The optimal reflux amount is expediently determined in preliminary experiments.

The optimal reflux ratio for the process according to the invention is determined in a known manner so that, with an economic optimum in terms of the power to be used for the separation of the lower and higher alcohol present in the system, an optimum is achieved in terms of the purity of the lower alcohol to be discharged at the top and of the solution of the higher alkoxide in the higher alcohol to be taken off at the bottom.

The lower alcohol taken off at the top, i.e. the substream of the top condensate that is discharged, is generally of high purity and can be reused without further distillation. Only the excess portion of the top condensate which is not needed to set the reflux amount is discharged from the system. The remaining portion of the top condensate is recycled to the top of the column as reflux.

The reactive distillation column typically has a bottoms circuit. In one embodiment, a substream of the solution of the higher metal alkoxide in the higher alcohol that is taken off at the bottom of the column is recycled to the bottom of the column, while a further substream of the solution of the higher metal alkoxide in the higher alcohol that is taken off at the bottom of the column is discharged from the process. In a further embodiment, a substream from the bottoms circuit is recycled to the bottom of the column, while a further substream is withdrawn from the bottoms circuit, preferably downstream of the evaporator, and discharged from the process.

The reactive distillation column has an evaporator which is integrated into the column bottom, or preferably an evaporator which is incorporated into a bottoms circuit. A substream of the solution of the higher metal alkoxide taken off at the bottom of the column is supplied via a bottoms circuit to the evaporator and is then recycled to the column as a heated, possibly two-phase fluid stream. Examples of suitable evaporators include reboilers, natural circulation evaporators, forced circulation evaporators and forced circulation flash evaporators.

In forced circulation evaporators, a pump is used to convey the liquid to be evaporated through the heater. The vapor/liquid mixture obtained is then recycled to the column.

In forced circulation flash evaporators, a pump is likewise used to convey the liquid to be evaporated through the heater. A superheated, liquid recycle stream is obtained which is expanded into the bottom of the column. The pressure on the solution of the metal alkoxide that is taken off from the column and recycled to the column is increased by superheating. The superheated recycle stream is expanded via a flow-limiting means. As a result, the liquid is superheated above its boiling point in relation to the pressure within the column.

When the superheated liquid passes through the flow-limiting means and re-enters the column, the liquid undergoes abrupt evaporation. This abrupt evaporation proceeds with a considerable increase in volume and leads to an acceleration of the fluid stream entering the column. Advantageously, the flow-limiting means is arranged directly before the re-entry of the superheated liquid into the column, or even within it.

As flow-limiting means, preference is given to using an orifice plate, a valve, a throttle, a perforated plate, a nozzle, a capillary or combinations thereof, in particular a valve. For example, a rotary plug valve can be used. It is particularly preferable when the opening characteristic of the flow-limiting means is adjustable. In this way, the pressure in the evaporator can always be kept above the boiling pressure of the liquid, based on the pressure within the column, even in the event of altered flow rates, as can arise for example during start-up and shutdown processes.

It is advantageous that by operating the evaporator in forced circulation or forced circulation flash mode, an increased flow rate of the liquid in the heating apparatus, for example the tube bundle of the heat exchanger, is achieved compared to operation using natural circulation. As a result of the increased flow rate, there is improved heat transfer between heat exchanger and heated liquid, which in turn contributes to avoiding local instances of overheating.

The pump to be used in the forced circulation or forced circulation flash evaporators is preferably arranged between the withdrawal conduit and the evaporator.

In a preferred embodiment, the column has a forced circulation evaporator and the higher alcohol is fed in liquid form into the feed to the forced circulation evaporator.

Alternatively or in addition to the bottom circulation evaporator, the bottom the heated directly, for example by means of a reboiler.

The bottom temperature of the reactive distillation column determines, for a given pressure, the concentration of the higher metal alkoxide in the solution taken off at the bottom of the column or from the bottoms circuit. The temperature and thus the concentration are expediently chosen such that the higher metal alkoxide always remains in solution in the bottom. The bottom temperature is for example set by an evaporator and/or direct heating of the bottom.

The process according to the invention may be conducted either under standard pressure or else under elevated or reduced pressure. It is advantageous to operate the reactive distillation column at a pressure of from 0.2 to 10 bar absolute. The reactive distillation column is preferably operated at ambient pressure, for example 1 bar absolute.

The equilibrium position of the reaction is temperature-dependent when preparing some alkoxides. In these cases, high temperatures may advantageously bring about a higher conversion. It may also be advantageous to carry out the process according to the invention under elevated pressure, such as for example at least 1.5 bar absolute, at least 2.5 bar absolute, or release 5.0 bar absolute.

The process according to the invention can be carried out either continuously or batchwise. The process according to the invention is preferably carried out continuously.

Within the reactive distillation column, the reaction equilibrium is constantly re-established as a result of the constant mass transfer and the changing concentrations within the gas phase and the liquid phase, which enables a high conversion. When starting up the column, the lower alcohol can be supplied to the column top to adjust the amount of the reflux of the lower alcohol, with the stripping section and bottom being filled with the higher alcohol. In addition, lower alcohol may be added to the higher alcohol.

After the operating temperature has been reached, the solution of the lower metal alkoxide is then supplied. New lower alcohol is formed continuously during the conversion.

In a further embodiment, the reactive distillation column is filled with the higher alcohol prior to starting up and this higher alcohol is initially also used as reflux. After the operating temperature has been reached, the solution of the lower metal alkoxide is then supplied.

The vapor taken off at the top of the column or its condensate typically consists of essentially pure lower alcohol. The condensate can be discharged without further purification and supplied for example to the preparation of lower metal alkoxides or solutions thereof.

The solution of the higher metal alkoxide that is taken off at the bottom of the column and/or from the bottoms circuit typically consists essentially of the higher alcohol and the higher metal alkoxide. The solution of the higher metal alkoxide can therefore be used further as such, optionally after cooling in a heat exchanger.

Alternatively, the higher alcohol may be separated off from the higher metal alkoxide. This can be done by evaporation.

BRIEF DESCRIPTION OF FIGURES

The invention is illustrated further by the appended figures and the following examples.

Figure 1:
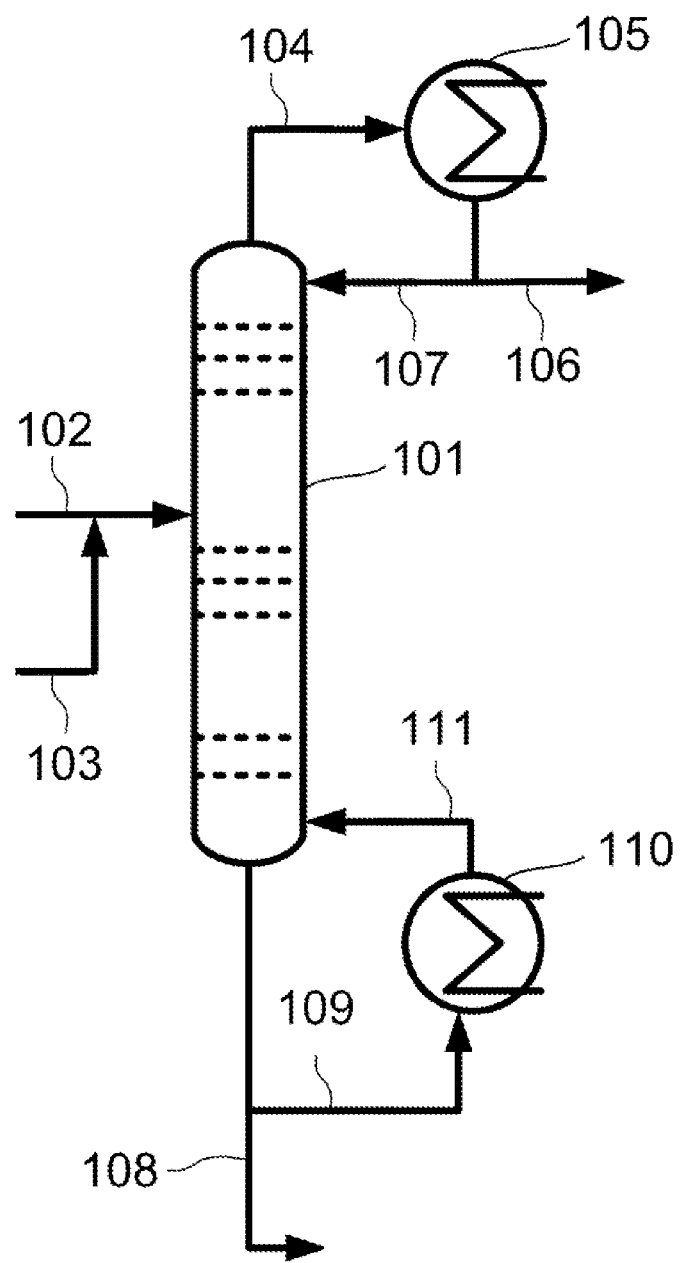
FIG. 1 shows a comparison plant suitable for the preparation of metal alkoxides.

According to FIG. 1, the plant comprises a reactive distillation column 101. Into this is fed a solution of a lower metal alkoxide via conduit 102 together with a higher alcohol from conduit 103.

At the top of column 101, a vapor comprising lower alcohol is taken off via conduit 104 and condensed in condenser 105. A first substream of the condensed vapor is discharged from the process via conduit 106, while a second substream of the condensed vapor is recycled to the top of the column via conduit 107.

A solution of the higher metal alkoxide in the higher alcohol is taken off at the bottom of the column. A first substream of the solution of the higher metal alkoxide is discharged from the process via conduit 108, while a second substream of the solution of the higher metal alkoxide is recycled to the bottom of the column via conduit 109, evaporator 110 and conduit 111.

Figure 2:
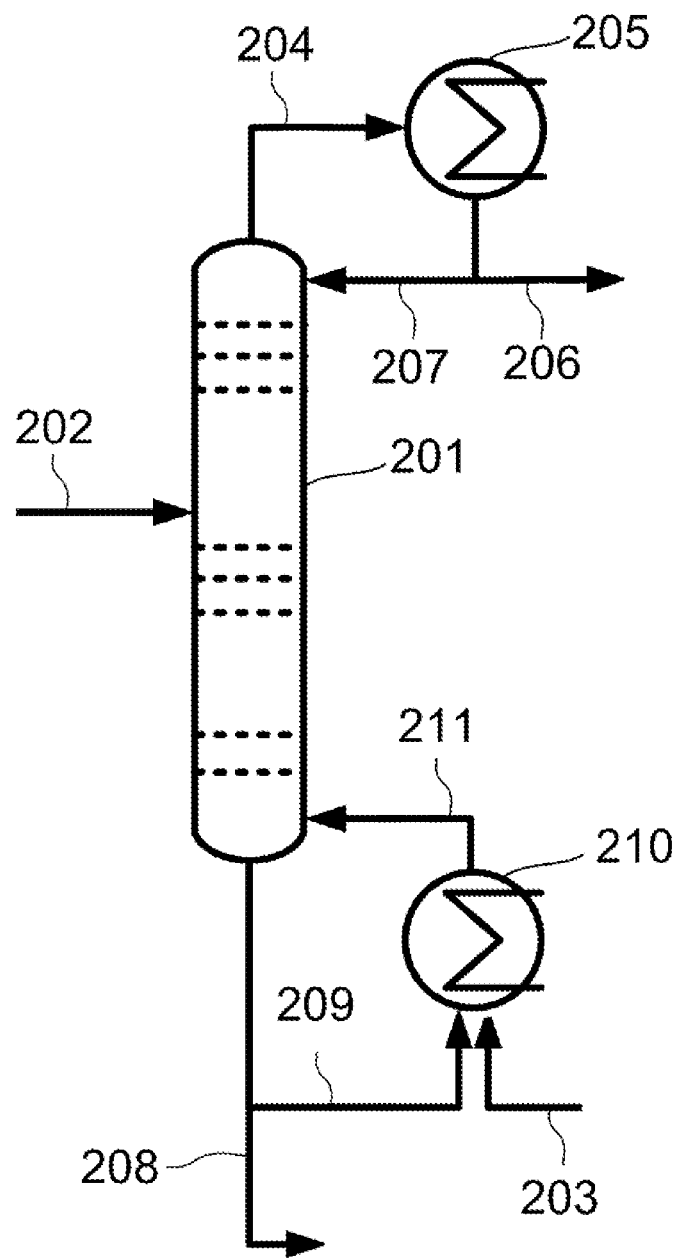
FIG. 2 shows a plant suitable for the preparation of metal alkoxides by means of the process according to the invention.

According to FIG. 2, the plant comprises a reactive distillation column 201. Into this is fed a solution of a lower metal alkoxide via conduit 202. A higher alcohol is fed into the bottoms circuit via conduit 203 and evaporator 210.

At the top of column 201, a vapor comprising lower alcohol is taken off via conduit 204 and condensed in condenser 205. A first substream of the condensed vapor is discharged from the process via conduit 206, while a second substream of the condensed vapor is recycled to the top of the column via conduit 207.

A solution of the higher metal alkoxide in the higher alcohol is taken off at the bottom of the column. A first substream of the solution of the higher metal alkoxide is discharged from the process via conduit 208, while a second substream of the solution of the higher metal alkoxide is recycled, together with the higher alcohol from conduit 203, to the bottom of the column via conduit 209, evaporator 210 and conduit 211.

Examples

Experiments were conducted for the preparation of sodium alkoxides by means of transalcoholization from sodium methoxide and higher alcohols, the higher alcohols used being isopropanol, 2-butanol and 2-methyl-2-butanol.
Methods
A. Determination of the Concentration of the Higher Alcohol in the Top Condensate To determine the content of higher alcohol in the top condensate, a sample was taken, 1,4-dioxane as internal standard was added and the sample was analyzed for its alcohol content by gas chromatography (RTX-5 Amine separating column, length 30 m, internal diameter 0.32 mm, film thickness 1.5 µm). The detection limit was approx. 500 mg/kg.

B. Determination of the Methanol Concentration in the Bottoms Discharge
B.1 Higher Alcohol: Isopropanol or 2-Butanol To determine the methanol content in the bottom of the column, 150 mg (when using isopropanol as higher alcohol) or 60 mg (when using 2-butanol) of a sample were weighed into a 22.5 ml headspace glass vessel.

1 ml of tap water was added to the sample, and the sample was sealed gas-tight with an aluminum cap and analyzed by headspace GC (DB-1 separating column, length 30 m, internal diameter 0.25 mm, film thickness 1.0 μm). Quantification was effected using the standard addition method. The detection limit was less than 100 mg/kg.

In the standard addition method, the sample is subjected to a multiple determination, for example a double determination. Here, a specific amount of the substance to be determined (the higher alcohol) is added multiple times to each sample and the sample is measured after each addition. The increase in the substance signal is ascertained. The concentration of the higher alcohol in the original sample can be calculated by linear regression.

The solubility of the samples must be tested in advance. If two phases form, the amount weighed in must be reduced.

B.2 Higher Alcohol: 2-Methyl-2-Butanol

To determine the methanol content in the bottom of the column, 500 mg of a sample were taken and allowed to cool to room temperature. The sample was mixed with 1 ml of water and 0.5 mg of tert-butanol in dioxane (1 ml, as internal standard), a drop of phosphoric acid was added thereto and the sample was diluted with 3 ml of dioxane (without internal standard) in order to obtain a diluted sample. In the case of solid samples, these were melted at 60° C. before mixing with water, tert-butanol, phosphoric acid and dioxane. The diluted sample was analyzed for its alcohol content by gas chromatography (DB-1 separation column, length 30 m, internal diameter 0.25 mm, film thickness 1.0 μm). The detection limit was approx. 200 mg/kg.

C. Determination of the Alkoxide Concentration in the Bottoms Discharge

To determine the alkoxide in the bottom of the column, a sample was taken and the total content of bases consisting of alkoxide, hydroxides and carbonate was determined by titration in 2-propanol with trifluoromethanesulfonic acid (0.1 mol/l in 2-propanol). The amount of hydroxides and carbonate was determined by means of volumetric Karl Fischer titration (KFT), since these constituents react with the KF components in the KFT and form water. The contribution of hydroxides and carbonates is subtracted from the total content of bases in order to ascertain the content of alkoxide.

Examples 1 to 5 and Comparative Examples 1 to 3

The examples were carried out in a plant which comprised an 80-tray glass bubble-cap tray column and a forced circulation flash evaporator. Tables 1A and 1B show the specific parameters of the examples. The evaporator was heated with a commercial thermostat (Julabo HT6) with a maximum heating power of 5700 W. The diameter of the column was 50 mm. Sodium methoxide (30% by weight in methanol) was fed into the column from the side. To avoid heat losses, the column was heated isothermally with an electric guard heater.

The higher alcohol was fed either upstream of the evaporator or to a tray in the stripping section or together with sodium methoxide from the side into the column. The amount of higher metal alkoxide or methanol in the solution of the higher metal alkoxide taken off at the bottom was determined.

The vapor was discharged at the top of the column and condensed in a condenser. The amount of higher alcohol in the top condensate was determined.

Comparative example 1 was initially performed like example 1. Once a steady state had been established, the feed of isopropanol upstream of the evaporator was halted and isopropanol was instead fed in together with sodium methoxide. The composition of the top condensate and of the sodium isopropoxide taken off at the bottom was determined after re-establishing the steady state.

Comparative example 2 was initially performed like example 2. Once a steady-state had been established, the feed of sec-butanol upstream of the evaporator was halted and sec-butanol was instead fed in together with sodium methoxide. The composition of the top condensate and of the sodium sec-butoxide taken off at the bottom was determined after re-establishing the steady state.

Comparative example 3 was performed analogously to example 5, with the difference that 2-methyl-2-butanol was not fed in upstream of the evaporator but instead together with sodium methoxide to tray 30. The composition of the top condensate and of the sodium 2-methyl-2-butoxide taken off at the bottom was determined after establishing the steady state.

TABLE 1A

Experimental test data for examples 1 and 2 and comparative examples 1 and 2.

| | Example 1 | Comparative example 1 | Example 2 | Comparative example 2 | | | |
|---|---|---|---|---|---|---|---|
| | | | | Version 1 | Version 2 | Version 3 | Version 4 |
| Higher alcohol | Isopropanol | | | 2-Butanol | | | |
| Na methoxide feed [kg/h] | 0.23 | 0.23 | 0.49 | 0.49 | 0.49 | 0.49 | 0.49 |
| Na methoxide feed point | Tray 40 | Tray 40 | Tray 30 | Tray 30 | Tray 30 | Tray 30 | Tray 30 |
| Higher alcohol feed [kg/h] | 1.226 | 1.125 | 1.814 | 1.742 | 1.800 | 1.874 | 1.918 |
| Higher alcohol feed point | Upstream of evaporator | Tray 40 | Upstream of evaporator | Tray 30 | Tray 30 | Tray 30 | Tray 30 |
| Top takeoff [kg/h] | 0.171 | 0.180 | 0.427 | 0.420 | 0.418 | 0.424 | 0.428 |
| Bottom takeoff [kg/h] | 1.286 | 1.172 | 1.869 | 1.809 | 1.871 | 1.94 | 1.977 |
| Bottoms circuit [kg/h] | 150 | 150 | 150 | 150 | 150 | 150 | 150 |
| Reflux [kg/h] | 1.341 | 1.343 | 0.700 | 0.700 | 0.835 | 0.900 | 1.001 |
| Reflux ratio | 7.84 | 7.46 | 1.64 | 1.67 | 2.00 | 2.12 | 2.34 |
| Ratio of feed/reflux | 0.172 | 0.171 | 0.700 | 0.700 | 0.587 | 0.544 | 0.4905 |
| T (column top) [° C.] | 63.0 | 62.2 | 62.2 | 62.6 | 62.1 | 62.2 | 62.3 |
| T (column bottom) [° C.] | 83.8 | 83.8 | 103 | 103 | 103 | 103 | 103 |
| T (feed) [° C.] | 47.9 | 54.5 | 52.5 | 54.0 | 54.0 | 54.0 | 54.5 |

TABLE 1A-continued

Experimental test data for examples 1 and 2 and comparative examples 1 and 2.

|  | Example 1 | Comparative example 1 | Example 2 | Comparative example 2 | | | |
|---|---|---|---|---|---|---|---|
|  |  |  |  | Version 1 | Version 2 | Version 3 | Version 4 |
| Top pressure [mbar, absolute] | 949 | 949 | 949.5 | 949.5 | 949.5 | 949.6 | 949.4 |
| Column differential pressure [mbar] | 81.3 | 82.2 | 73.8 | 76.2 | 78.2 | 79.8 | 82.5 |
| Alkoxide in bottom [% by weight] | 7.8 | 9.2 | 14.4 | 14.5 | 14.1 | 13.5 | 13.5 |
| Methanol in bottom [% by weight] | 0.04 | 2.0 | 0.07 | 0.7 | 0.4 | 0.2 | 0.1 |
| Higher alcohol in top condensate [% by weight] | 0.15 | 0.4 | 0.360 | 1.04 | n.d. * | n.d. * | n.d. * |

* n.d.: below the detection limit

TABLE 1B

Experimental test data for Examples 3 to 5 and Comparative Example 3.

|  | Example 3 | Example 4 | Example 5 | | | Comparative example 3 | |
|---|---|---|---|---|---|---|---|
|  |  |  | Version 1 | Version 2 | Version 3 | Version 1 | Version 2 |
| Higher alcohol | 2-Butanol | | | 2-Methyl-2-butanol | | | |
| Na methoxide feed [kg/h] | 0.49 | 0.49 | 0.15 | 0.225 | 0.10 | 0.15 | 0.10 |
| Na methoxide feed point | Tray 30 | Tray 30 | Tray 30 | Tray 30 | Tray 30 | Tray 30 | Tray 30 |
| Higher alcohol feed [kg/h] | 1.864 | 1.861 | 1.036 | 1.23 | 0.531 | 0.469 | 0.325 |
| Higher alcohol feed point | Upstream of evaporator | Tray 15 | Upstream of evaporator | Upstream of evaporator | Upstream of evaporator | Tray 30 | Tray 30 |
| Top takeoff [kg/h] | 0.430 | 0.432 | 0.139 | 0.187 | 0.091 | 0.099 | 0.068 |
| Bottom takeoff [kg/h] | 1.912 | 1.916 | 1.057 | 1.278 | 0.569 | 0.511 | 0.342 |
| Bottoms circuit [kg/h] | 150 | 150 | 150 | 150 | 150 | 150 | 150 |
| Reflux [kg/h] | 0.860 | 0.840 | 0.835 | 1.000 | 1.000 | 1.330 | 1.000 |
| Reflux ratio | 2.00 | 1.94 | 7.19 | 5.35 | 14.62 | 10.10 | 19.56 |
| Ratio of feed/reflux | 0.570 | 0.583 | 0.150 | 0.225 | 0.075 | 0.150 | 0.075 |
| T (column top) [° C.] | 62.4 | 62.3 | 62.7 | 63 | 62.6 | 62.3 | 62.3 |
| T (column bottom) [° C.] | 103 | 103 | 103.7 | 104.2 | 104.5 | 106.5 | 106.5 |
| T (feed) [° C.] | 50.3 | 50.0 | 47.4 | 49.9 | 47.7 | 52.2 | 51 |
| Top pressure [mbar, absolute] | 949.5 | 949.5 | 949.3 | 949.3 | 949.1 | 949.8 | 949.9 |
| Column differential pressure [mbar] | 78.7 | 78.2 | 81.8 | 83.7 | 88.9 | 80.6 | 88.1 |
| Alkoxide in bottom [% by weight] | 13.4 | 13.4 | 9.6 | 12.1 | 10.1 | 16.7 | 17.4 |
| Methanol in bottom [% by weight] | 0.012 | 0.09 | 0.27 | 0.76 | 0.04 | 0.82 | 0.16 |
| Higher alcohol in top condensate [% by weight] | 0.3 | n.d.* | 8.85 | 1.19 | 6.28 | n.d.* | n.d.* |

*n.d.: below the detection limit

It can be seen from the comparison of example 1 with comparative example 1 that feeding the higher alcohol in upstream of the evaporator, compared to feeding in the higher alcohol together with the lower alkoxide to tray 40 of the column, results in a lower methanol concentration in the bottom for the same ratio of feed to reflux.

It can in turn be seen from the comparison of example 2 with comparative example 2 (version 1) that feeding the higher alcohol in upstream of the evaporator, compared to feeding in the higher alcohol together with the lower alkoxide to tray 30 of the column, results in a lower methanol concentration in the bottom for the same ratio of feed to reflux. Even with an increase in the reflux in versions 2 to 4 of comparative example 2 from 0.7 kg/h to 1.0 kg/h, the methanol concentration on the bottom only falls to 0.1% by weight, compared to 0.07% by weight in example 2.

In example 3, the higher alcohol was fed in upstream of the evaporator. In example 4, the higher alcohol was fed in to tray 15 in the stripping section. In comparative example 2 (version 2), the higher alcohol was fed in together with the lower alkoxide to tray 30. The reflux ratios were comparable in these three experiments. It can be seen that the methanol concentration in the bottom in examples 3 and 4 was significantly lower than in comparative example 2 (version 2). This shows that feeding the higher alcohol in upstream of the evaporator or in the stripping section of the column, compared to feeding in the higher alcohol together with the lower alkoxide to tray 30 of the column, results in a lower methanol concentration in the bottom for the same ratio of feed to reflux. It is particularly advantageous to feed the higher alcohol in upstream of the evaporator.

It can be seen from the comparison of example 5, version 1, with comparative example 3, version 1, that feeding the higher alcohol in upstream of the evaporator, compared to feeding in the higher alcohol together with the lower alkoxide to tray 30 of the column, results in a lower methanol concentration in the bottom for the same ratio of feed to reflux. This can also be seen from the comparison of example 5, version 3, with comparative example 3, version 2.

The specific heating power of the preparation process was additionally determined for selected examples on the basis of the temperature of the heating oil (KORASILON M 10 oil; spec. heat capacity cp (120° C.): 1.74 kJ/(kg K)) in the feed and in the return. The results are shown in table 2.

TABLE 2

| | Example 2 | Comparative example 2, version 4 | Example 5, Version 2 | Comparative example 3, version 1 |
|---|---|---|---|---|
| Specific heating power | | | | |
| Methanol in bottom [% by weight] | 0.07 | 0.1 | 0.76 | 0.82 |
| Feed oil temperature [° C.] | 120.1 | 122.8 | 122.5 | 127.7 |
| Return oil temperature [° C.] | 115.4 | 117.6 | 117.5 | 121.2 |
| ΔT feed/return [° C.] | 4.7 | 5.2 | 5 | 6.5 |
| Oil mass flow rate [kg/h] | 331.0 | 322.3 | 319.1 | 190.1 |
| Evaporator heating power [W] | 752 | 810 | 771 | 597 |
| Specific heating power [J/g] | 10.1 | 10.9 | 18.0 | 25.2 |

It can be seen that the process according to the invention for a comparable separation task requires a lower specific heating power than when the higher alcohol is fed in together with the lower metal alkoxide.

The invention claimed is:

1. A process for preparing metal alkoxides by means of transalcoholization, wherein
   a lower metal alkoxide is fed via a side feed into a reactive distillation column comprising a top, a bottom, a rectifying section situated above the feed and a stripping section situated below the feed;
   a higher alcohol is fed into the stripping section, the bottom and/or a bottoms circuit of the column;
   a solution of a higher metal alkoxide in the higher alcohol is taken off at the bottom of the column and/or from the bottoms circuit; and
   a vapor comprising lower alcohol is taken off at the top of the column, the vapor is at least partially condensed and a substream of the condensate is recycled to the top of the column as reflux;
   wherein the higher alcohol has a higher boiling point than the lower alcohol.

2. The process according to claim 1, wherein the higher alcohol is fed into the bottom and/or the bottoms circuit of the column in liquid form.

3. The process according to claim 1, wherein the solution of the higher metal alkoxide comprises not more than 1.0% by weight of the lower alcohol, based on the total weight of the solution of the higher metal alkoxide.

4. The process according to claim 1, wherein the solution of the higher metal alkoxide comprises 3% to 60% by weight of the higher metal alkoxide, based on the total weight of the solution of the higher metal alkoxide.

5. The process according to claim 1, wherein the column has a forced circulation evaporator and the higher alcohol is fed in liquid form into the feed to the forced circulation evaporator.

6. The process according to a claim 1, wherein the top condensate comprises not more than 0.8% by weight of the higher alcohol, based on the total weight of the top condensate.

7. The process according to claim 1, wherein the lower metal alkoxide is fed in as a solution in the lower alcohol and the solution comprises 20% to 40% by weight of the lower metal alkoxide, based on the total weight of the solution of the lower metal alkoxide.

8. The process according to a claim 1, wherein the lower metal alkoxide is an alkali metal alkoxide.

9. The process according to claim 8, wherein the lower metal alkoxide is a sodium alkoxide or a potassium alkoxide.

10. The process according to claim 9, wherein the lower metal alkoxide is sodium methoxide or potassium methoxide.

11. The process according to claim 1, wherein the higher alcohol is selected from isopropanol, sec-butanol, 2-methyl-2-butanol, tert-butanol, 2-methyl-2-pentanol, 3-methyl-3-pentanol, 3-ethyl-3-pentanol, 2-methyl-2-hexanol and 3-methyl-3-hexanol.

* * * * *